United States Patent
Kück et al.

(10) Patent No.: US 6,200,271 B1
(45) Date of Patent: Mar. 13, 2001

(54) BI-DIRECTIONAL PARTIAL RE-BREATHING METHOD

(75) Inventors: Kai Kück, Hamburg (DE); Joseph A. Orr, Park City, UT (US); Michael B. Jaffe, Cheshire, CT (US); Dinesh G. Haryadi, Bangalore (IN)

(73) Assignee: NTC Technology Inc., Wilmington, DE (US)

( * ) Notice: Subject to any disclaimer, the term of this patent is extended or adjusted under 35 U.S.C. 154(b) by 0 days.

(21) Appl. No.: 09/150,135

(22) Filed: Sep. 9, 1998

(51) Int. Cl.[7] .................................................. A61B 5/08

(52) U.S. Cl. .................. 600/532; 600/529; 600/500; 128/204.12

(58) Field of Search ..................... 600/500–504, 600/526, 528–538; 128/204.12–204.23, 897–899, 920–925

(56) References Cited

U.S. PATENT DOCUMENTS

| | | |
|---|---|---|
| 4,221,224 | 9/1980 | Clark . |
| 4,463,764 | 8/1984 | Anderson et al. . |
| 5,060,656 | 10/1991 | Howard . |
| 5,069,220 | 12/1991 | Casparie et al. . |
| 5,117,674 | 6/1992 | Howard . |
| 5,178,155 | 1/1993 | Mault . |
| 5,285,794 | 2/1994 | Lynch . |
| 5,299,579 | 4/1994 | Gedeon et al. . |
| 5,402,796 | 4/1995 | Packer et al. . |
| 5,632,281 | * 5/1997 | Rayburn .............. 600/538 |
| 5,836,300 | * 11/1998 | Mault .................. 600/532 |
| 5,971,934 | * 10/1999 | Scherer et al. ........ 600/526 |

FOREIGN PATENT DOCUMENTS

WO 98/12963    4/1998    (WO) .

OTHER PUBLICATIONS

H. Blomquist et al., A Non–Invasive Technique for Measurement of Lung Perfusion, Intensive Care Medicine 1986; 12:172.

R.J. Bosman et al, Non–Invasive Pulimonary Blood Flow Measurement by Means of $CO_2$ Analysis Of Expiratory Gases, Intensive Care Medicine 1991, 17:98–102.

A. Gedeon, *Non–Invasive Pulmonary Blood Flow for Optimal Peep*, ICOR AB, Ulvsundavagen 178 B, S–161 30 Bromma, Sweden, pp. 49–58.

Capek, J.M., Noninvasive Measurement of Cardiac Output Using Partial $CO_2$ Rebreathing [Dissertation], Rensselaer Polytechnic Institute (1988) 28:351 p. (due to large number of pages, only table of contents and abstract have been copied).

Capek, J.M., et al., Noninvasive Measurement of Cardiac Output Using Partial $CO_2$ Rebreathing, IEEE Trans. Biomed. Eng. (1988) 35(9):653–61.

Davies, Gerald G., et al., Continuous Fick cardiac output compared to thermodilution cardiac output, Critical Care Medicine (1986) 14(10):881–85.

Elliott, C. Gregory, et al., Complications of Pulmonary Artery Catheterization in the Care of Critically Ill Patients, Chest (1979) 76:647–52.

(List continued on next page.)

Primary Examiner—Cary O'Connor
Assistant Examiner—Michael Astorino
(74) Attorney, Agent, or Firm—Trask Britt (57) ABSTRACT

A re-breathing method for determining pulmonary capillary blood flow that accounts for changes in the carbon dioxide content of a patient. The carbon dioxide elimination and partial pressure of end tidal carbon dioxide of the patient are measured prior to re-breathing, during re-breathing, and after re-breathing. A rate of change of carbon dioxide content of the venous blood of the patient is then calculated. The rate of change is then employed in calculating the pulmonary capillary blood flow of the patient.

59 Claims, 4 Drawing Sheets

OTHER PUBLICATIONS

Fick, A., *Über die Messung des Blutquantums in den Herzventrikeln*, Sitzungsbericht der Physikalisch–Medizinischen Gesellschaft zu Würzburg (1870) 36 (2 pages).

Gama de Abreu, Marcelo, et al., Measurement of Pulmonary Capillary Blood Flow for Trending Mixed Venous Blood Oxygen Saturation and Oxygen Delivery, Crit. Care Med (1998) vol. 26, No. 1 (Suppl), A106, Abstract #238 (1 page).

Gama de Abreu, Marcelo, et al., Is the Partial $CO_2$ Rebreathing Technique a Useful Tool for Trending Pulmonary Capillary Blood Flow During Adjustments of Peep?, Crit. Care Med (1998) vol. 26, No. 1 (Suppl), A106, Abstract #237, (1 page).

Gama de Abreu, et al., Partial carbon dioxide rebreathing: A reliable technique for noninvasive measurement of non-shunted pulmonary capillary blood flow, Crit. Care Med. (1997) 25(4):675–83.

Gedeon, A., et al., Noninvasive Cardiac Output Determined with a New Method Based on Gas Exchange Measurements and Carbon Dioxide Rebreathing: A Study in Animals/Pigs, J.Clin. Monit. (1992) 8(4):267–78.

Gedeon, A., et al., A new method for noninvasive bedside determination of pulmonary blood flow, Med. & Biol. Eng. & Comput. (1980) 18:411–418.

Guyton, A.E., et al., Measurement of cardiac output by the direct Fick method, In: *Cardiac output and its regulation*, W.B. Saunders Company (1973) 21–39.

Kyoku, I., et al. Measurement of cardiac output by Fick method using $CO_2$ analyzer Servo, Kyobu Geka, Japanese Journal of Thoracic Surgery (1988) 41(12):966–70.

Lynch, J., et al., Comparison of a modified Fick method with thermodilution for determining cardiac output in critically ill patients on mechanical ventilation, Intensive Care Med. (1990) 16:248–51.

Mahutte, C. Kees, et al., Relationship of Thermodilution Cardiac Output to Metabolic Measurements and Mixed Venous Oxygen Saturation, Chest (1993) 104(4):1236–42.

Miller, D.M., et al., A Simple Method for the Continuous Noninvasive Estimate of Cardiac Output Using the Maxima Breathing System. A Pilot Study, Anaesth. Intens. Care (1997) 25(1):23–28.

Österlund, B., et al., A new method of using gas exchange measurements for the noninvasive determination of cardiac output: clinical experiences in adults following cardiac surgery, Acta Anaesthesiol Scand (1995) 39:727–32.

Sackner, Marvin A., Measurement of cardiac output by alveolar gas exchange, Handbook of Physiology~The Respiratory System IV, Chapter 13, 233–55.

Spalding, H. K., et al., Carbon Dioxide ($CO_2$) Elimination Rate Accurately Predicts Cardiac Output, Anesthesiology (1997) 87(3A) (1 page).

Sprung, Charles L., et al., Ventricular Arrhythmias During Swan–Ganz Catheterization of the Critically Ill, Chest (1981) 79:413–15.

Taskar, V., et al., Dynamics of Carbon Dioxide Elimination Following Ventilator Resetting, Chest (1995) 108:196–202.

Winkler, Tilo, et al., Pulmonary Capillary Blood Flow by Partial $CO_2$ Rebreathing: A Simulation Study Using a Bicompartmental Model of Gas Exchange, Crit Care Med (1998) vol. 26, No. 1 (Suppl), A105, Abstract #234 (1 page).

* cited by examiner

BI-DIRECTIONAL PARTIAL RE-BREATHING METHOD

BACKGROUND OF THE INVENTION

1. Field of the Invention

The present invention relates to methods of non-invasively determining the pulmonary capillary blood flow of a patient. Particularly, the present invention relates to re-breathing techniques for measuring the pulmonary capillary blood flow of a patient. More particularly, the methods of the present invention account for changes in the carbon dioxide content of the venous blood of a patient that may occur during re-breathing.

2. Background of Related Art

Cardiac output, the volume of blood that is pumped by the heart over a set period of time, includes two components, pulmonary capillary blood flow ($Q_{pcbf}$) and intrapulmonary shunt ($Q_s$). Pulmonary capillary blood flow is the volume of blood (typically measured in liters) that participates in the exchange of blood gases over a set period of time (typically one minute). Cardiac output is typically measured during surgery or while a patient is under intensive care and indicates the cardiovascular condition of the patient and the patient's response to medical intervention. Conventionally, cardiac output has been measured by both invasive and non-invasive techniques.

Indicator dilution, an exemplary invasive, typically intermittent technique for measuring cardiac output, includes introducing a predetermined amount of an indicator into a single point of the bloodstream of a patient and analyzing blood downstream from the point of introduction to obtain a time vs. dilution curve. Thermodilution, in which room temperature or colder saline solution, which may also be referred to as "cold" saline, is employed as the indicator, is a widely employed type of indicator dilution. Typically, the cold saline is introduced into the right heart bloodstream of a patient through a thermodilution catheter, which includes a thermistor at an end thereof. The thermistor is employed to measure the temperature of the blood after it has passed through the right heart, or downstream from the point at which the cold saline is introduced. A thermodilution curve is then generated from the data, from which the cardiac output of the patient may be derived. Thermodilution and other indicator dilution techniques are, however, somewhat undesirable due to the potential for harm to the patient that is associated by inserting and maintaining such catheters in place.

Conventional, so-called "non-invasive" techniques for determining the cardiac output of a patient typically include a pulmonary capillary blood flow measurement according to the Fick principle: the rate of uptake of a substance by or release of a substance from blood at the lung is equal to the blood flow past the lung and the content difference of the substance at each side of the lung. The Fick principle may be represented in terms of oxygen ($O_2$) by the following formula:

$$Q=VO_2/(CaO_2-CvO_2),$$

where Q is the cardiac output of the patient, $VO_2$ is the volume of oxygen consumed by the patient per unit of time, $CaO_2$ is the $O_2$ content of the arterial, or oxygenated, blood of the patient, and $CvO_2$ is the $O_2$ content of the venous, or de-oxygenated, blood of the patient. The oxygen Fick principle may be employed in calculating the cardiac output of a patient either intermittently or continuously. The intrapulmonary shunt flow may also be estimated and subtracted from the cardiac output to determine the pulmonary capillary blood flow of the patient.

An exemplary method of determining the cardiac output of a patient by monitoring $VO_2$ is disclosed in Davies et al., Continuous Fick cardiac output compared to thermodilution cardiac output, *Crit. Care Med.* 1986; 14:881–885 ("Davies"). The method of Davies includes continually measuring the $O_2$ content of samples of gas inspired and expired by a patient, the oxygen saturation ($SvO_2$) of the patient's venous blood, and oxygen saturation ($SaO_2$) of the patient's arterial blood. The $O_2$ measurements are made by a metabolic gas monitor, and $VO_2$ calculated from these measurements. $SaO_2$ is measured by pulse oximetry. $SvO_2$ is directly measured by a pulmonary artery ("PA") catheter. Each of these values is then incorporated into the oxygen Fick equation to determine the cardiac output of the patient. Although the method of Davies may be employed to intermittently or continuously determine the cardiac output of a patient, it is somewhat undesirable from the standpoint that accurate $VO_2$ measurements are typically difficult to obtain, especially when the patient requires an elevated fraction of inspired oxygen ($FiO_2$). Moreover, since the method disclosed in Davies requires continual measurement of $SvO_2$ with a pulmonary artery catheter, it is an invasive technique.

Due in part to the ease with which the carbon dioxide elimination ($VCO_2$) of a patient may be accurately measured, $VCO_2$ measurements are widely employed in methods of non-invasively determining the pulmonary capillary blood flow of a patient. Since the respiratory quotient (RQ) is the ratio of carbon dioxide elimination to the amount of oxygen inhaled, $VCO_2$ may be substituted for $VO_2$ according to the following equation:

$$VO_2=VCO_2/RQ.$$

Alternatively, a modification of the Fick principle, which is based on the exchange of carbon dioxide ($CO_2$) in the lungs of a patient, has been employed to calculate the pulmonary capillary blood flow of the patient. The carbon dioxide Fick equation, which represents the Fick principle in terms of $CO_2$ elimination and exchange, follows:

$$Q=VCO_2/(CvCO_2-CaCO_2),$$

where $VCO_2$ is the carbon dioxide elimination of the patient, $CvCO_2$ is the content, or concentration, of $CO_2$ in the venous blood of the patient, and $CaCO_2$ is the content, or concentration, of $CO_2$ in the arterial blood of the patient. The difference between $CvCO_2$ and $CaCO_2$ is typically referred to as the arterial-venous gradient, or "AV gradient".

The carbon dioxide Fick equation has been employed to non-invasively determine the pulmonary capillary blood flow and cardiac output of a patient on an intermittent basis. The carbon dioxide elimination of the patient may be non-invasively measured as the difference per breath between the volume of carbon dioxide inhaled during inspiration and the volume of carbon dioxide exhaled during expiration, and is typically calculated as the integral of the carbon dioxide signal times the rate of flow over an entire breath. The volume of carbon dioxide inhaled and exhaled may each be corrected for any deadspace.

The partial pressure of end-tidal carbon dioxide ($PetCO_2$ or $etCO_2$) is also measured in re-breathing processes. The partial pressure of end tidal carbon dioxide, after correcting for any deadspace, is typically assumed to be approximately equal to the partial pressure of carbon dioxide in the alveoli ($PACO_2$) of the patient or, if there is no intrapulmonary shunt, the partial pressure of carbon dioxide in the arterial blood of the patient ($PaCO_2$).

Re-breathing is typically employed either to non-invasively estimate the carbon dioxide content of mixed venous blood (in total re-breathing) or to obviate the need to know the carbon dioxide content of the mixed venous blood (by partial re-breathing) or determine the partial pressure of carbon dioxide in the patient's venous blood ($PvCO_2$). Re-breathing processes typically include the inhalation of a gas mixture which includes carbon dioxide. During re-breathing, the $CO_2$ elimination of the patient is less than during normal breathing. Re-breathing during which the $CO_2$ elimination decreases to near zero is typically referred to as total re-breathing. Re-breathing that causes some decrease, but not a total cessation of $CO_2$ elimination, is typically referred to as partial re-breathing.

Figure 1:
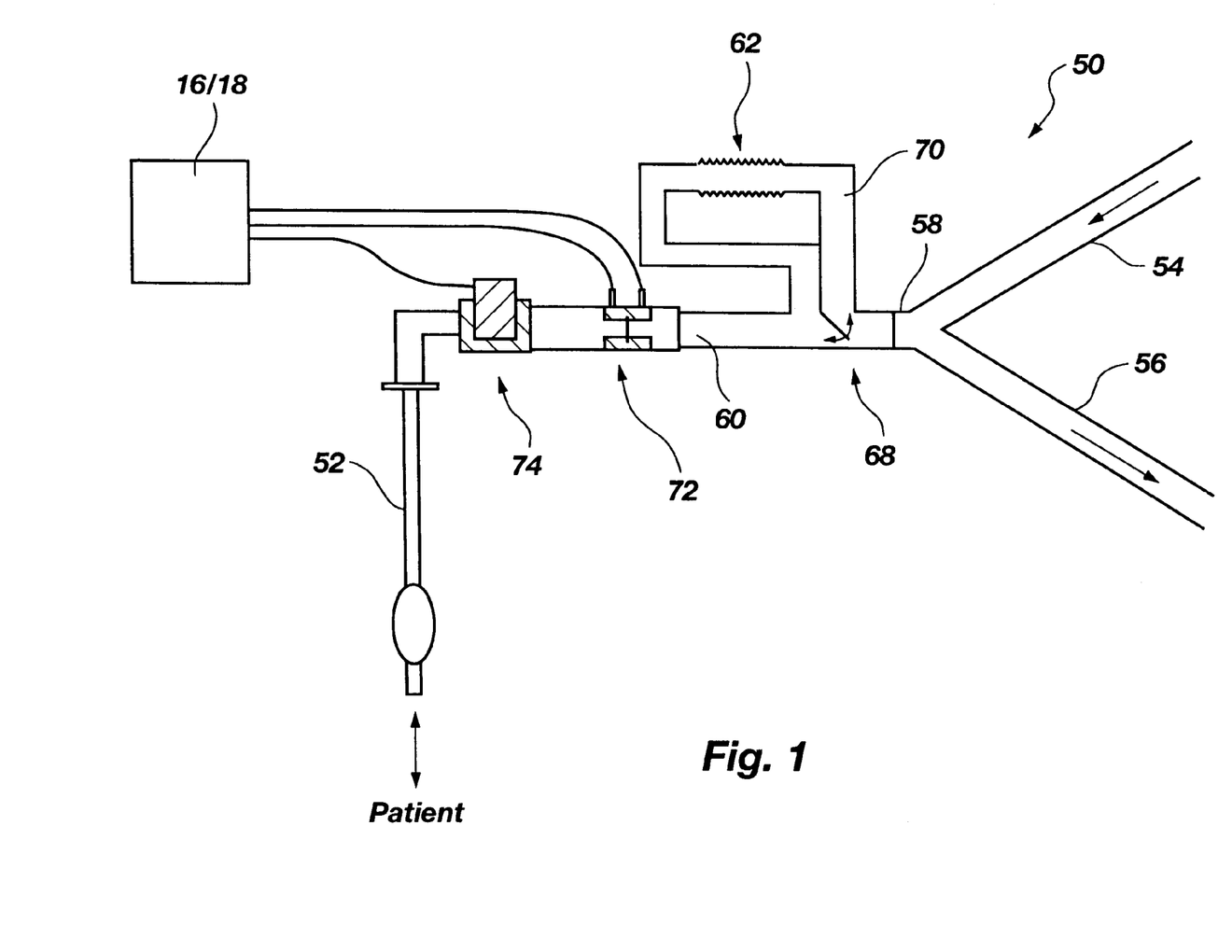
FIG. 1 is a schematic representation of an exemplary re-breathing circuit that may be employed with the methods of the present invention.

Re-breathing is typically conducted with a re-breathing circuit, which causes a patient to inhale a gas mixture that includes carbon dioxide. FIG. 1 schematically illustrates an exemplary re-breathing circuit 50 that includes a tubular airway 52 that communicates air flow to and from the lungs of a patient. Tubular airway 52 may be placed in communication with the trachea of the patient by known intubation processes, or by connection to a breathing mask positioned over the nose and/or mouth of the patient. A flow meter 72, which is typically referred to as a pneumotachometer, and a carbon dioxide sensor 74, which is typically referred to as a capnometer, are disposed between tubular airway 52 and a length of hose 60, and are exposed to any air that flows through re-breathing circuit 50. Both ends of another length of hose, which is referred to as deadspace 70, communicate with hose 60. The two ends of deadspace 70 are separated from one another by a two-way valve 68, which may be positioned to direct the flow of air through deadspace 70. Deadspace 70 may also include an expandable section 62. A Y-piece 58, disposed on hose 60 opposite flow meter 72 and carbon dioxide sensor 74, facilitates the connection of an inspiratory hose 54 and an expiratory hose 56 to re-breathing circuit 50 and the flow communication of the inspiratory hose 54 and expiratory hose 56 with hose 60. During inhalation, gas flows into inspiratory hose 54 from the atmosphere or a ventilator (not shown). During normal breathing, valve 68 is positioned to prevent inhaled and exhaled air from flowing through deadspace 70. During re-breathing, valve 68 is positioned to direct the flow of exhaled and inhaled gases through deadspace 70.

During total re-breathing, substantially all of the gas inhaled by the patient was expired during the previous breath. During total re-breathing, the partial pressure of end-tidal carbon dioxide is typically assumed to be equal to the partial pressure of carbon dioxide in the venous blood ($PvCO_2$) of the patient, as well as to the partial pressure of carbon dioxide in the arterial blood ($PaCO_2$) and the partial pressure of carbon dioxide in the alveolar blood ($PACO_2$) of the patient. Total re-breathing processes are based on the assumption that neither pulmonary capillary blood flow nor the content of carbon dioxide in the venous blood of the patient ($CvCO_2$) changes substantially during the re-breathing process. The partial pressure of carbon dioxide in blood may be converted to the content of carbon dioxide in blood by means of a carbon dioxide dissociation curve. The carbon dioxide form of the Fick equation, in which $CvCO_2$ and $CaCO_2$ are variables, may be employed to determine pulmonary capillary blood flow.

In partial re-breathing, the patient inhales a mixture of gases exhaled during the previous breath and "fresh" gases. Thus, the patient does not inhale as much carbon dioxide as would be inhaled during a total re-breathing process. Conventional partial re-breathing processes typically employ a differential form of the carbon dioxide Fick equation to determine the pulmonary capillary blood flow of the patient, which does not require knowledge of the carbon dioxide content of the mixed venous blood. This differential form of the carbon dioxide Fick equation considers measurements of carbon dioxide elimination ($VCO_2$), $CvCO_2$, and the content of carbon dioxide in the alveolar blood of the patient ($CACO_2$) during both normal breathing and the re-breathing process as follows:

$$Q_{pcbf\,BD} = \frac{V_{CO_{2B}} - V_{CO_{2D}}}{(C_V CO_{2B} - C_V CO_{2D}) - (C_A CO_{2B} - C_A CO_{2D})},$$

where $VCO_{2B}$ and $VCO_{2D}$ are the carbon dioxide elimination of the patient before re-breathing and during the re-breathing process, respectively, $CvCO_{2B}$ and $CvCO_{2D}$ are the contents of $CO_2$ of the venous blood of the patient before re-breathing and during the re-breathing process, respectively, and $CACO_{2B}$ and $CACO_{2D}$ are the contents of $CO_2$ in the alveolar blood (i.e., the blood in the capillaries that surround the alveoli) of the patient before re-breathing and during the re-breathing process, respectively. The alveolar partial pressures of carbon dioxide may then be converted to the carbon dioxide contents of the patient's alveolar blood by means of a carbon dioxide dissociation curve. During conventional re-breathing processes, the pulmonary capillary blood flow and $CvCO_2$ of a patient are assumed to remain substantially unchanged. The latter assumption causes the $CvCO_2$ terms of the preceding equation to cancel each other, but is somewhat undesirable because it may introduce error into the cardiac output determination.

Alternative differential Fick methods of measuring pulmonary capillary blood flow or cardiac output have also been employed. Such differential Fick methods typically include a brief change of $PetCO_2$ and $VCO_2$ in response to a change in effective ventilation. This brief change can be accomplished by adjusting the respiratory rate, inspiratory and/or expiratory times, or tidal volume. A brief change in effective ventilation may also be effected by adding $CO_2$, either directly or by re-breathing. An exemplary differential Fick method that has been employed, which is disclosed in Gedeon, A. et al. in 18 *Med. & Biol. Eng. & Comput.* 411–418 (1980), employs a period of increased ventilation followed immediately by a period of decreased ventilation.

Accordingly, an accurate, non-invasive method of determining the pulmonary capillary blood flow or cardiac output of a patient is needed that compensates for changes in the carbon dioxide content of the venous blood of a patient during re-breathing.

SUMMARY OF THE INVENTION

The methods of the present invention address the foregoing needs.

The re-breathing method of the present invention includes determining the volume of carbon dioxide exhaled by a patient, which estimates the carbon dioxide elimination ($VCO_2$) of the patient, before ($VCO_{2B}$), during ($VCO_{2D}$), and after ($VCO_{2A}$) either total or partial re-breathing. The end tidal partial pressure of carbon dioxide is also measured for each of the "before", "during" and "after" phases. From the end tidal partial pressures, the partial pressure of carbon dioxide in the alveoli of the lungs of the patient that participate in the exchange of oxygen for carbon dioxide in the blood, which are typically referred to as "perfused" alveoli, is determined. A carbon dioxide dissociation curve is employed with the end tidal carbon dioxide partial pressure measurements, as known in the art, to convert these partial pressures to the content of carbon dioxide in the blood of the "exit" end of capillaries that surround the perfused alveoli (Cc'CO$_2$), which is typically referred to as the "end-capillary" blood, for each of the "before", "during" and "after" phases.

The differences between the carbon dioxide elimination before re-breathing and during re-breathing, which difference is also referred to as "$\Delta VCO_{2BD}$", and during re-breathing and after re-breathing, which difference is also referred to as "$\Delta VCO_{2DA}$", are determined. The differences between the content of end capillary carbon dioxide in the capillary blood before and during re-breathing, which difference is also referred to as "$\Delta CACO_{2BD}$", and during re-breathing and alter re-breathing, which difference is also referred to as "$\Delta CACO_{2DA}$", are also determined.

These differences are then employed to calculate the rate at which the content of carbon dioxide in the venous blood of the patient changes. An exemplary equation for estimating the rate of change in the content of carbon dioxide in the patient's venous blood (k), which assumes that the change is linear with time and, therefore, that the rate of change is constant, or the change is linear with respect to time, follows:

$$k = \frac{\Delta V_{CO_{2BD}} \cdot \Delta C_A CO_{2DA} - \Delta V_{CO_{2DA}} \cdot \Delta C_A CO_{2BD}}{\Delta V_{CO_{2BD}}(t_D - t_A) - \Delta V_{CO_{2DA}}(t_B - t_D)}.$$

Alternatively, the change in carbon dioxide content in the venous blood may be assumed to follow a curve of some other shape that is reasonably based on the character of the change in carbon dioxide content and that could be approximated by methods such as an exponential curve, or the curve of a polynomial, an artificial neural network, or a radial basis function.

Once the rate of change in the content of carbon dioxide in the patient's blood has been estimated, the pulmonary capillary blood flow ($Q_{pcbf}$) of the patient may be accurately determined as follows:

$$Q_{pcbf} = \frac{V_{CO_{2B}} + V_{CO_{2A}} - 2V_{CO_{2D}}}{k \cdot (t_B + t_A - 2t_D) - (C_A CO_{2B} + C_A CO_{2A} - 2C_A CO_{2D})},$$

where $t_B$, $t_D$ and $t_A$ represent the times at which VCO$_2$ was determined during the "before", "during" and "after" phases, respectively.

The methods of the present invention may also be applied to alternative differential Fick methods of measuring pulmonary capillary blood flow or cardiac output, which require a brief change of PetCO$_2$ and VCO$_2$ in response to a change in effective ventilation. This brief change in effective ventilation can be accomplished by adjusting the respiratory rate, inspiratory and/or expiratory times, or tidal volume. A brief change in effective ventilation may also be effected by adding CO$_2$, either directly or by re-breathing. An exemplary differential Fick method, which is disclosed in Gedeon, A. et al. in 18 *Med. & Biol. Eng. & Comput.* 411–418 (1980), employs a period of increased ventilation followed immediately by a period of decreased ventilation.

Other advantages of the present invention will become apparent through a consideration of the ensuing description, the accompanying drawings, and the appended claims.

DETAILED DESCRIPTION OF THE PREFERRED EMBODIMENTS

The present invention includes a method of estimating the rate at which the carbon dioxide content of the venous blood of a patient changes. The rate of change may be employed to determine the amount of change in the carbon dioxide content of the venous blood of the patient or the pulmonary capillary blood flow of the patient. Formulae are employed in accordance with the method of the present invention to determine the rate of change in the carbon dioxide content of the venous blood of the patient, the amount of change in the carbon dioxide content, and the pulmonary capillary blood flow.

Derivation of Formulae in the Methods

A differential form of the carbon dioxide Fick equation, similar to that employed in conventional partial re-breathing techniques, which is based on carbon dioxide elimination and CO$_2$ content measurement taken during normal breathing, before re-breathing and during the re-breathing process, follows:

$$Q_{pcbf\,BD} = \frac{V_{CO_{2B}} - V_{CO_{2D}}}{(C_V CO_{2B} - C_V CO_{2D}) - (C_A CO_{2B} - C_A CO_{2D})},$$

or $$Q_{pcbf\,BD} = \frac{\Delta V_{CO_{2B}}}{\Delta C_V CO_{2B} - C_A CO_{2BD}},$$

where CvCO$_{2B}$ is the CO$_2$ content of the venous blood of the patient prior to re-breathing, or in the "before" phase, and CvCO$_{2D}$ is the CO$_2$ content of the venous blood of the patient during rebreathing, or in the "during" phase.

Another differential form of the carbon dioxide Fick equation, which is based on carbon dioxide elimination and CO$_2$ content measurements made during the re-breathing process and after re-breathing, which may also be employed to determine the pulmonary capillary blood flow of a patient, follows:

$$Q_{pcbf\,DA} = \frac{V_{CO_{2D}} - V_{CO_{2A}}}{(C_V CO_{2D} - C_V CO_{2A}) - (C_A CO_{2D} - C_A CO_{2A})}$$

or $$Q_{pcbf\,DA} = \frac{\Delta V_{CO_{2DA}}}{\Delta C_V CO_{2DA} - \Delta C_A CO_{2DA}},$$

where $CvCO_{2A}$ is the $CO_2$ content of the venous blood of the patient after re-breathing, or in the "after" phase.

Assuming that pulmonary capillary blood flow does not change between the "before", "during", and "after" phases, the two preceding differential forms of the carbon dioxide Fick equation may be combined to yield the following differential form of the carbon dioxide Fick equation:

$$Q_{pcbf} = \frac{\Delta V_{CO_{2BD}} - \Delta V_{CO_{2DA}}}{(\Delta C_V CO_{2BD} - \Delta C_V CO_{2DA}) - (\Delta C_A CO_{2BD} - \Delta C_A CO_{2DA})}.$$

Since $CvCO_2$ may change over time, an accurate non-invasive Fick-based determination of the pulmonary capillary blood flow of a patient should include an estimation of the rate at which $CvCO_2$ changes. With an exemplary assumption that changes in $CvCO_2$ are substantially linear over the re-breathing cycle and, therefore, that the rate of change is constant, the rate of change in $CvCO_2$ (k) may be represented by the following equation:

$$k = \frac{\Delta C_V CO_2}{\Delta t}.$$

Alternatively, the change in carbon dioxide content of the venous blood may be assumed to substantially follow a curve of some other shape that is reasonably based on the character of the change in carbon dioxide content, such as an exponential curve, wherein the rate of change would also be exponential, or the curve of a polynomial. As another alternative, the rate of change in the content of carbon dioxide in the venous blood may be approximated by an artificial neural network or a radial basis function, as known in the art.

When the change in $CvCO_2$ is assumed to be linear with respect to time and, therefore, the rate of change of $CvCO_2$ is assumed to be constant, the change in $CvCO_2$ between the "before" and "during" phases and between the "during" and "after" phases can be expressed by the following equations:

$$\Delta CvCO_{2BD} = k(t_B - t_D)$$

and $$\Delta CvCO_{2DA} = k(t_D - t_A),$$

where $t_D$, $t_B$ and $t_A$ represent the times at which the "before", "duing" and "after" phases respectively occur.

The foregoing equations for the change in $CvCO_2$ may be substituted into the differential form of the carbon dioxide Fick equation that considers the breathing of a patient during each of the "before", "during" and "after" phases and the "$\Delta$" terms expanded to yield the following form of the carbon dioxide Fick equation, which accounts for any changes in $CvCO_2$ and is, therefore, useful in the methods of the present invention:

$$Q_{pcbf} = \frac{V_{CO_{2B}} + V_{CO_{2A}} - 2 \cdot V_{CO_{2D}}}{k \cdot (t_B + t_A - 2t_D) - (C_A CO_{2B} + C_A CO_{2A} - 2 \cdot C_A CO_{2D})}.$$

If, however, $t_D - t_B = t_A - t_D$, then $t_A + t_B = 2 \cdot t_D$, and it would not be necessary to calculate k, as k would be multiplied by zero.

Accordingly, if $t_D - t_B = t_A - t_D$, the following equation could be employed to determine the pulmonary capillary blood flow of a patient:

$$Q_{pcbf} = \frac{V_{CO_{2B}} + C_{CO_{2A}} - 2 \cdot V_{CO_{2D}}}{-(C_A CO_{2B} + C_A CO_{2A} - 2 \cdot C_A CO_{2D})}.$$

Due to the assumption that the pulmonary capillary blood flow of a patient remains substantially constant from the "before" phase to the "after" phase, the differential carbon dioxide Fick equations for determining cardiac output over the "before" and "during" phases ($Q_{pcbfBD}$) and for determining cardiac output over the "during" and "after" phases ($Q_{pcbfDA}$) may be employed to estimate k, the rate of change in $CvCO_2$, as follows:

$$Q_{pcbfBD} = Q_{pcbfDA},$$

thus, $$\frac{\Delta V_{CO_{2BD}}}{\Delta C_V CO_{2BD} - \Delta C_A CO_{2BD}} = \frac{\Delta V_{CO_{2DA}}}{\Delta C_V CO_{2DA} - \Delta C_A CO_{2DA}},$$

which may be rearranged as:

$$\Delta VCO_{2BD} \cdot \Delta CvCO_{2DA} - \Delta VCO_{2DA} \cdot \Delta CvCO_{2BD} = \Delta VCO_{2BD} \cdot \Delta CACO_{2DA} - \Delta VCO_{2DA} \cdot \Delta CACO_{2BD}.$$

The equations for $\Delta CvCO_{2BD}$ and $\Delta CvCO_{2BD}$ are then substituted into the preceding equation to yield the following equation:

$$\Delta VCO_{2BD} \cdot k(t_D - t_A) - \Delta VCO_{2DA} \cdot k(t_B - t_D) = \Delta VCO_{2BD} \cdot \Delta CACO_{2DA} - \Delta VCO_{2DA} \cdot \Delta CACO_{2BD},$$

which may be rearranged to provide the following equation for k, the rate of change in $VCO_2$:

$$k = \frac{\Delta V_{CO_{2BD}} \cdot \Delta C_A CO_{2DA} - \Delta V_{CO_{2DA}} \cdot \Delta C_A CO_{2BD}}{\Delta V_{CO_{2BD}}(t_D - t_A) - \Delta V_{CO_{2DA}}(t_B - t_D)}.$$

Measuring Respiratory, Blood and Blood Gas Profile Parameters

Figure 2:
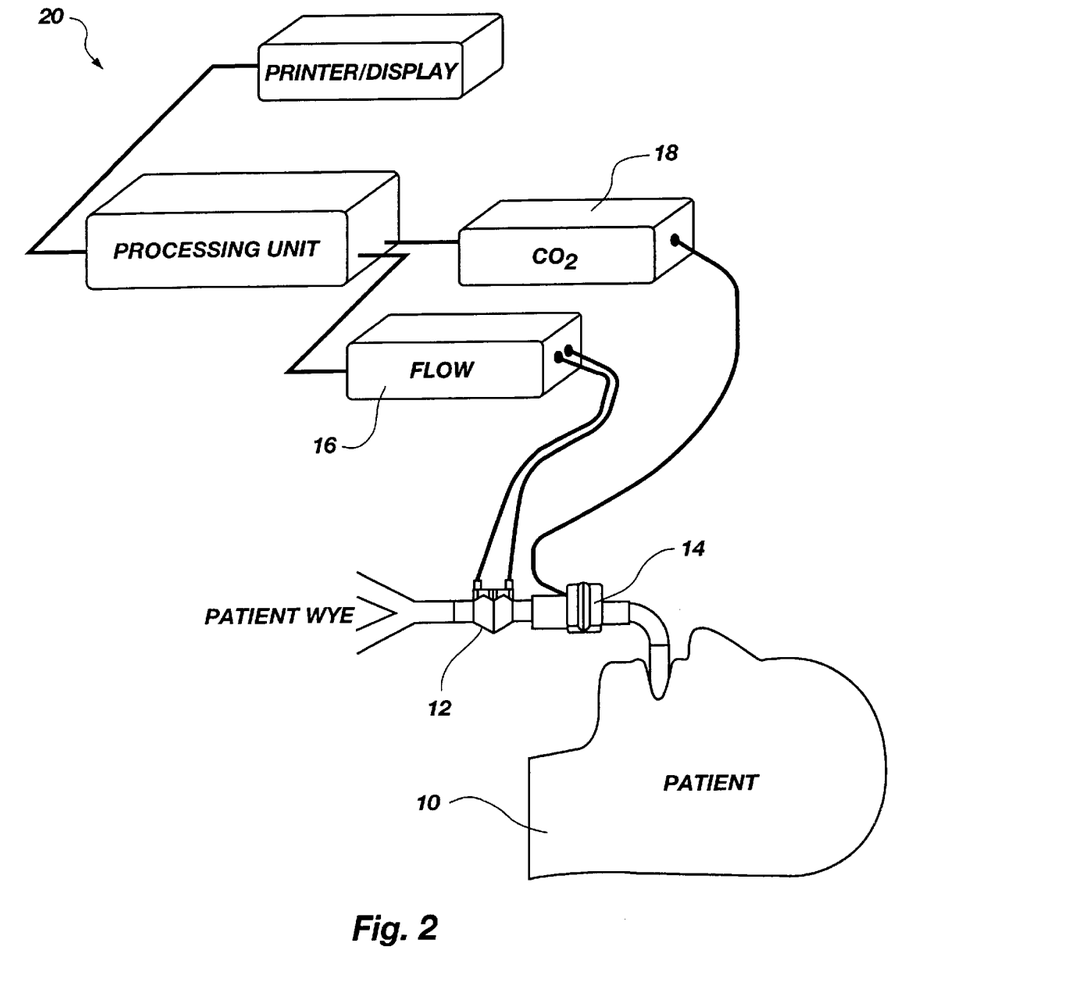
FIG. 2 is a schematic representation which illustrates the componentry that may be utilized to measure respiratory profile parameters that are employed in the methods of the present invention.

With reference to FIG. 2, a preferred embodiment of the method of the present invention includes non-invasively measuring the flow rates and carbon dioxide ($CO_2$) fraction of gas mixtures (e.g., air) that are inhaled and exhaled by a patient 10 over the course of the patient's breathing while known re-breathing techniques are employed. A flow sensor 12 of a known type, such as the differential-pressure type respiratory flow sensors manufactured by Novametrix Medical Systems Inc. ("Novametrix") of Wallingford, Conn. (e.g, the Pediatric/Adult Flow Sensor (Catalog No. 6717) or the Neonatal Flow Sensor (Catalog No. 6718)), as well as respiratory flow sensors based on other operating principles and manufactured or marketed by Novametrix or others, which may be operatively attached to a ventilation apparatus (not shown), may be employed to measure the flow rates of the breathing of patient 10. A $CO_2$ sensor 14, such as the CAPNOSTAT® $CO_2$ sensor and a complementary airway adapter (e.g., the Pediatric/Adult Single Patient Use Airway Adapter (Catalog No. 6063), the Pediatric/Adult Reusable Airway Adapter (Catalog No. 7007), or the Neonatal/

Pediatric Reusable Airway Adapter (Catalog No. 7053)), which are manufactured by Novametrix, as well as other main stream or side stream $CO_2$ sensors manufactured or marketed by Novametrix or others, may be employed to measure the $CO_2$ fraction of gas mixtures that are inhaled and exhaled by patient 10. Flow sensor 12 and $CO_2$ sensor 14 are connected to a flow monitor 16 and a $CO_2$ monitor 18, respectively, each of which may be operatively associated with a computer 20 so that data from the flow and $CO_2$ monitors 16 and 18, representative of the signals from each of flow sensor 12 and $CO_2$ sensor 14, may be detected by computer 20 and processed according to programming (e.g., by software) thereof. Preferably, raw flow and $CO_2$ signals from the flow monitor and $CO_2$ sensor are filtered to remove any significant artifacts. As several respiratory flow and $CO_2$ pressure measurements are made, the respiratory flow and $CO_2$ pressure data may be stored by computer 20. Thus, cardiac output may be calculated, in accordance with the carbon dioxide Fick equation or by any other suitable equation known in the art, by computer 20.

Each breath, or breathing cycle, of patient 10 may be delineated, as known in the art, such as by continually monitoring the flow rate of the breathing of patient 10.

The patient's breathing is monitored before re-breathing, during re-breathing, and after re-breathing, which are also referred to as the "before", "during" and "after" phases, respectively. FIG. 1 illustrates an exemplary apparatus that may be employed in re-breathing processes to detect the amount of $CO_2$ exhaled by the patient, from which $VCO_2$ and $CvCO_2$ may be determined.

When the breathing of a patient 10 (see FIG. 2) is monitored before re-breathing, two-way valve 68 is positioned to prevent the flow of inhaled and exhaled gas through deadspace 70. The duration of the "before" phase is preferably sufficient to obtain accurate $CO_2$ and flow measurements. The time at which the "before" phase occurs ($t_B$) is also determined. $t_B$ may be calculated as the average time of the "before" phase, or otherwise, as known in the art. As an example, if $t_B$ was the average time of the "before" phase, and the "before" phase started about 40 seconds after the initiation ($t_0$) of a re-breathing measurement and lasted until about 46 seconds after $t_0$, $t_B$ would be at about 43 seconds.

During re-breathing, two-way valve 68 is positioned to facilitate the flow of exhaled gases into and inhaled gases from deadspace 70, which, after the patient has exhaled, includes gases from the patient's previously exhaled breath. The "during" phase preferably continues for about 50 seconds. The time at which the "during" phase occurs ($t_D$) is also determined. $t_D$ may be calculated as the average time of the "during" phase, or otherwise, as known in the art, similar to the calculation of $t_B$.

After re-breathing, two-way valve 68 is repositioned to prevent the flow of gases through deadspace 70 as the patient breathes. The "after" phase may be of any duration sufficient to facilitate the accurate determination of $VCO_2$ and $CACO_2$. The time at which the "after" phase occurs ($t_A$) is also determined. $t_A$ may be calculated as the average time of the "after" phase, or otherwise, as known in the art, similar to the calculation of $t_B$.

Figure 3:
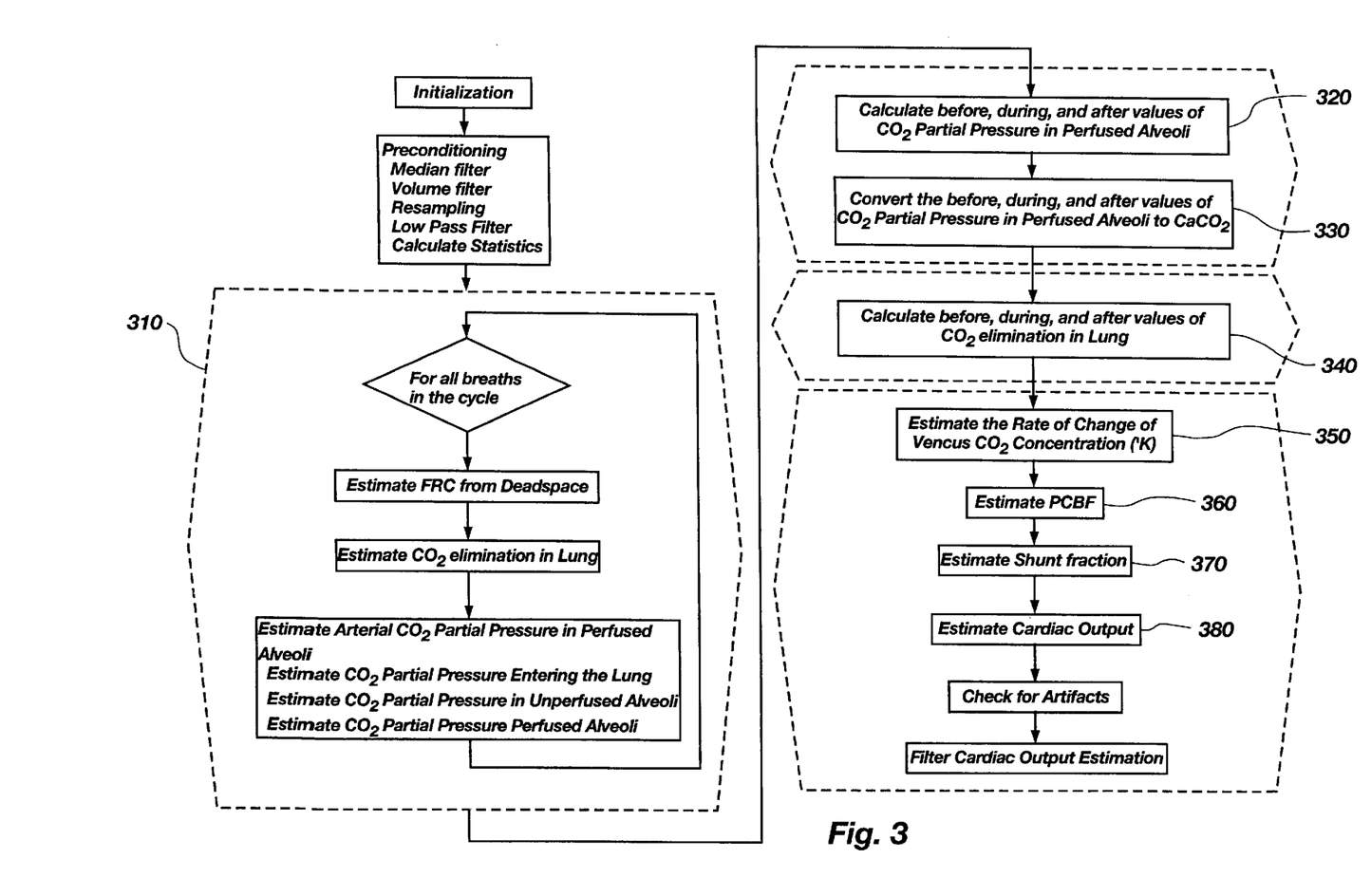
FIG. 3 is a flow chart that schematically illustrates the method of the present invention.

Referring to FIG. 2, and at reference 310 of FIG. 3, the amount of carbon dioxide exhaled by the patient during each of the "before", "during" and "after" phases is detected by carbon dioxide sensor 14 (reference 74 of FIG. 1) and monitored by $CO_2$ monitor 18. $CO_2$ monitor 18 generates signals that, along with respiratory flow signals generated by flow monitor 16 in response to the flow of inhaled and exhaled gases by flow sensor 12, may be employed to determine $VCO_2$, at reference 340 of FIG. 3, and the end tidal $CO_2$ partial pressure, at reference 320 of FIG. 3, as known in the art. At reference 330 of FIG. 3, the end tidal $CO_2$ partial pressure, which is assumed to estimate the partial pressure of carbon dioxide in the alveolar or end-capillary blood ($Pc'CO_2$) of the patient, may be employed with a carbon dioxide dissociation curve of a type known in the art to determine $CACO_2$.

Figure 4:
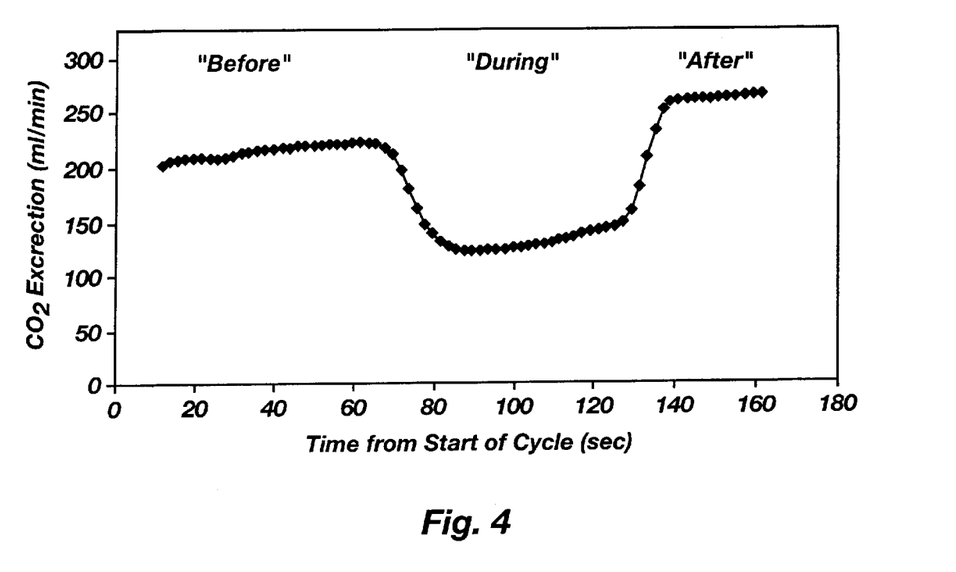
FIG. 4 is a line graph that illustrates the VCO$_2$ of a patient during each of the before, during, and after phases of the re-breathing method of the present invention.

The difference between the volume of carbon dioxide exhaled and the volume of carbon dioxide that is inhaled by a patient, which estimates the carbon dioxide elimination ($VCO_2$) of the patient, is determined before ($VCO_{2B}$), during ($VCO_{2D}$), and after ($VCO_{2A}$) re-breathing. FIG. 4 is a graph that illustrates $VCO_2$ during each of the before, during, and after phases of the re-breathing process of the present invention.

Figure 5:
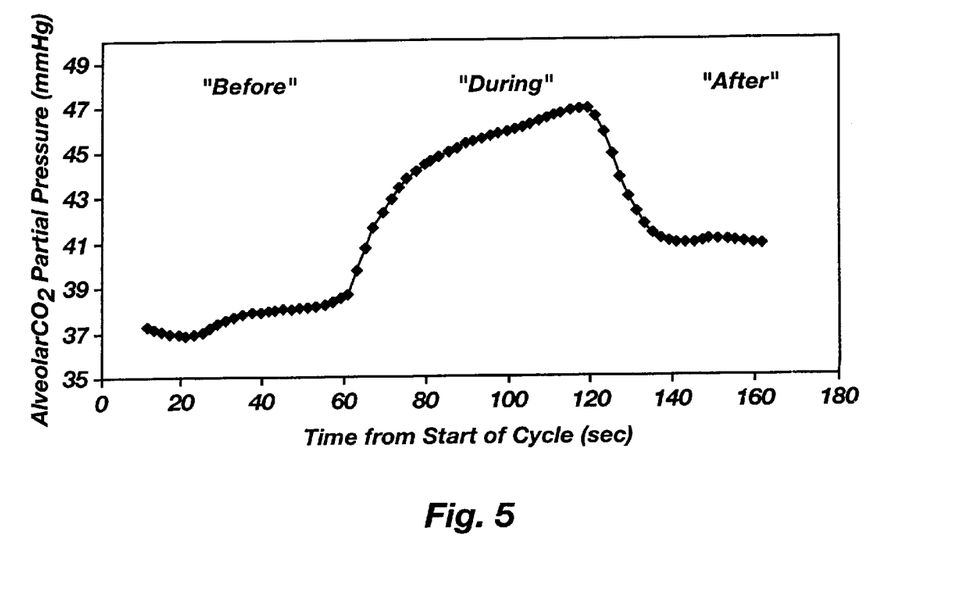
FIG. 5 is a line graph that illustrates the etCO$_2$ of a patient during each of the before, during, and after phases of the re-breathing method of the present invention.

The partial pressure of end tidal carbon dioxide ($PetCO_2$ or $etCO_2$) is also measured for each of the "before", "during" and "after" phases. As $etCO_2$, when corrected for parallel deadspace (of non-perfused alveoli), is assumed to be equal to the partial pressure of $CO_2$ in the alveoli ($PACO_2$), a carbon dioxide dissociation curve may be employed with the end tidal carbon dioxide partial pressure measurements, as known in the art, to determine the content of carbon dioxide in blood of the alveoli ($CACO_2$) of the lungs of the patient that participate in the exchange of blood gases, which alveoli are typically referred to as "perfused" alveoli, for each of the before, during, and after re-breathing phases. FIG. 5 is a graph that illustrates the $etCO_2$ measured during each of the before, during, and after phases of the re-breathing process of the present invention.

Determining Pulmonary Capillary Blood Flow

The differences between the carbon dioxide elimination before re-breathing and during re-breathing, which difference is also referred to as "$\Delta VCO_{2BD}$", and during re-breathing and after re-breathing, which difference is also referred to as "$\Delta VCO_{2DA}$", are determined. The differences between the content of carbon dioxide in the alveolar blood before and during re-breathing, which difference is also referred to as "$\Delta CACO_{2BD}$", and during re-breathing and after re-breathing, which difference is also referred to as "$\Delta CACO_{2DA}$", are also determined.

These differences are then employed, at reference 350 of FIG. 3, to calculate the rate at which the content of carbon dioxide in the venous blood of the patient changes. An exemplary equation for estimating the rate of change in the content of carbon dioxide in the patient's venous blood (k), which assumes that the change is linear with time and, therefore, that the rate of change is constant, follows:

$$k = \frac{\Delta V_{CO_{2BD}} \cdot \Delta C_A CO_{2DA} - \Delta V_{CO_{2DA}} \cdot \Delta C_A CO_{2BD}}{\Delta V_{CO_{2BD}}(t_D - t_A) - \Delta V_{CO_{2DA}}(t_B - t_D)}.$$

Once the rate of change in the content of carbon dioxide in the patient's blood has been estimated, the pulmonary capillary blood flow of the patient may be accurately determined, at reference 360 of FIG. 3, as follows:

$$Q_{pcbf} = \frac{V_{CO_{2B}} + V_{CO_{2A}} - 2V_{CO_{2D}}}{k \cdot (t_B + t_A - 2t_D) - (C_A CO_{2B} + C_A CO_{2A} - 2C_A CO_{2D})},$$

The intrapulmonary shunt flow of the patient or intrapulmonary shunt fraction of the cardiac output of the patient may also be determined, as known in the art, at reference 370 of FIG. 3. The cardiac output of the patient may then be determined, at reference 380 of FIG. 3, from the pulmonary capillary blood flow and intrapulmonary shunt flow of the patient, as known in the art.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed is:

1. A method of non-invasively determining pulmonary capillary blood flow of a patient, comprising:

measuring a before re-breathing carbon dioxide elimination and a before re-breathing partial pressure of end tidal carbon dioxide prior to a re-breathing phase;

measuring a during re-breathing carbon dioxide elimination and a during re-breathing partial pressure of end tidal carbon dioxide during said re-breathing phase; and measuring an after re-breathing carbon dioxide elimination and an after re-breathing partial pressure of end tidal carbon dioxide after said re-breathing phase.

2. The method of claim 1, further comprising determining a rate of change of a carbon dioxide content of venous blood of the patient.

3. The method of claim 2, further comprising:

determining a before re-breathing alveolar content of carbon dioxide from said before re-breathing partial pressure of end tidal carbon dioxide;

determining a during re-breathing alveolar content of carbon dioxide from said during re-breathing partial pressure of end tidal carbon dioxide; and determining an after re-breathing alveolar content of carbon dioxide from said after re-breathing partial pressure of end tidal carbon dioxide.

4. The method of claim 3, further comprising:

determining a before time of said before re-breathing carbon dioxide elimination;

determining a during time of said during re-breathing carbon dioxide elimination; and determining an after time of said after re-breathing carbon dioxide elimination.

5. The method of claim 2, further comprising:

determining a before time of said before re-breathing partial pressure of end tidal carbon dioxide;

determining a during time of said during re-breathing partial pressure of end tidal carbon dioxide; and determining an after time of said after re-breathing partial pressure of end tidal carbon dioxide.

6. The method of claim 3, further comprising:

calculating said rate of change by employing the following equation:

$$k = \frac{\Delta V_{CO_{2BD}} \cdot \Delta C_A CO_{2DA} - \Delta V_{CO_{2DA}} \cdot \Delta C_A CO_{2BD}}{\Delta V_{CO_{2BD}}(t_D - t_A) - \Delta V_{CO_{2DA}}(t_B - t_D)}.$$

where $\Delta VCO_{2BD}$ comprises a difference between said before re-breathing carbon dioxide elimination and said during re-breathing carbon dioxide elimination, $\Delta CACO_{2DA}$ comprises a difference between said during re-breathing alveolar content and said after re-breathing alveolar content, $\Delta VCO_{2DA}$ comprises a difference between said during re-breathing carbon dioxide elimination and said after re-breathing carbon dioxide elimination, $\Delta CACO_{2BD}$ comprises a difference between said before re-breathing alveolar content and said during re-breathing alveolar content, $t_B$ comprises a time of prior to said re-breathing phase, $t_D$ comprises a time during said re-breathing phase, and $t_A$ comprises a time after said re-breathing phase.

7. The method of claim 3, further comprising calculating pulmonary capillary blood flow with said before re-breathing carbon dioxide elimination, said during re-breathing carbon dioxide elimination, said after re-breathing carbon dioxide elimination, said before re-breathing alveolar content, said during re-breathing alveolar content, said after re-breathing alveolar content, and said rate of change.

8. The method of claim 4, further comprising calculating pulmonary capillary blood flow with said before re-breathing carbon dioxide elimination, said during re-breathing carbon dioxide elimination, said after re-breathing carbon dioxide elimination, said before re-breathing alveolar content, said during re-breathing alveolar content, said after re-breathing alveolar content, said before time, said during time, said after time, and said rate of change.

9. The method of claim 7, further comprising calculating said pulmonary capillary blood flow by employing the following equation:

$$Q_{pcbf} = \frac{V_{CO_{2B}} + V_{CO_{2A}} - 2V_{CO_{2D}}}{k \cdot (t_B + t_A - 2t_D) - (C_A CO_{2B} + C_A CO_{2A} - 2C_A CO_{2D})}.$$

10. The method of claim 2, wherein said rate of change is substantially constant.

11. The method of claim 2, wherein said rate of change is substantially exponential over time.

12. The method of claim 1, further comprising:

determining a before time of said before re-breathing carbon dioxide elimination;

determining a during time of said during re-breathing carbon dioxide elimination; and determining an after time of said after re-breathing carbon dioxide elimination.

13. The method of claim 12, wherein a difference between said during time and said before time is equal to a difference between said after time and said during time.

14. The method of claim 13, further comprising calculating pulmonary capillary blood flow by employing the following equation:

$$Q_{pcbf} = \frac{V_{CO_{2B}} + V_{CO_{2A}} - 2V_{CO_{2D}}}{-(C_A CO_{2B} + C_A CO_{2A} - 2C_A CO_{2D})}.$$

15. A method of non-invasively determining a pulmonary capillary blood flow of a patient, comprising:

determining a before re-breathing carbon dioxide elimination ($VCO_{2B}$) of the patient, a before re-breathing alveolar partial pressure of carbon dioxide ($PACO_{2B}$) of the patient, and a before time ($t_B$);

re-breathing to determine a during re-breathing carbon dioxide elimination ($VCO_{2D}$) of the patient, a during re-breathing alveolar partial pressure of carbon dioxide ($PACO_{2D}$) of the patient, and a during time ($t_D$);

determining an after re-breathing carbon dioxide elimination ($VCO_{2A}$) of the patient, an after re-breathing alveolar partial pressure of carbon dioxide ($PACO_{2A}$) of the patient, and an after time ($t_A$); and calculating a rate of change (k) of a carbon dioxide content of venous blood of the patient.

16. The method of claim 15, wherein said rate of change comprises a substantially linear change over time.

17. The method of claim 15, wherein said rate of change comprises a substantially exponential change over time.

18. The method of claim 15, wherein said calculating said rate of change comprises employing the following equation:

$$k = \frac{\Delta V_{CO_{2BD}} \cdot \Delta C_A CO_{2DA} - \Delta V_{CO_{2DA}} \cdot \Delta C_A CO_{2BD}}{\Delta V_{CO_{2BD}}(t_D - t_A) - \Delta V_{CO_{2DA}}(t_B - t_D)}.$$

19. The method of claim 18, further comprising calculating pulmonary capillary blood flow by the following equation:

$$Q_{pcbf} = \frac{V_{CO_{2B}} + V_{CO_{2A}} - 2V_{CO_{2D}}}{k \cdot (t_B + t_A - 2t_D) - (C_A CO_{2B} + C_A CO_{2A} - 2C_A CO_{2D})}.$$

20. The method of claim 15, wherein $t_D - t_B = t_A - t_D$.

21. The method of claim 20, further comprising calculating pulmonary capillary blood flow by the following equation:

$$Q_{pcbf} = \frac{V_{CO_{2B}} + V_{CO_{2A}} - 2V_{CO_{2D}}}{-(C_A CO_{2B} + C_A CO_{2A} - 2C_A CO_{2D})}.$$

22. A method of non-invasively determining a pulmonary capillary blood flow of a patient, comprising:

measuring a carbon dioxide elimination ($VCO_2$) of the patient before, during and after a re-breathing process; and determining an alveolar partial pressure of carbon dioxide ($PACO_2$) of the patient before, during and after said re-breathing process.

23. The method of claim 22, further comprising determining a time (t) of each of said before, said during, and said after said re-breathing process.

24. The method of claim 23, further comprising calculating a rate of change (k) of a content of carbon dioxide in venous blood of the patient.

25. The method of claim 24, wherein said calculating comprises employing the following equation:

$$k = \frac{\Delta V_{CO_{2BD}} \cdot \Delta C_A CO_{2DA} - \Delta V_{CO_{2DA}} \cdot \Delta C_A CO_{2BD}}{\Delta V_{CO_{2BD}}(t_D - t_A) - \Delta V_{CO_{2DA}}(t_B - t_D)}.$$

26. The method of claim 24, further comprising calculating pulmonary capillary blood flow ($Q_{pcbf}$).

27. The method of claim 26, wherein said calculating comprises employing the following equation:

$$Q_{pcbf} = \frac{V_{CO_{2B}} + V_{CO_{2A}} - 2V_{CO_{2D}}}{k \cdot (t_B + t_A - 2t_D) - (C_A CO_{2B} + C_A CO_{2A} - 2C_A CO_{2D})},$$

28. The method of claim 24, wherein said rate of change comprises a substantially linear change with respect to time.

29. The method of claim 24, wherein said rate of change comprises a substantially exponential change over time.

30. The method of claim 25, wherein $t_D - t_B = t_A - t_D$.

31. The method of claim 30, further comprising calculating pulmonary capillary blood flow by the following equation:

$$Q_{pcbf} = \frac{V_{CO_{2B}} + V_{CO_{2A}} - 2V_{CO_{2D}}}{-(C_A CO_{2B} + C_A CO_{2A} - 2C_A CO_{2D})}.$$

32. A method of determining a rate of change in carbon dioxide content of venous blood of a patient, comprising:

measuring a carbon dioxide elimination ($VCO_2$) of the patient before (B), during (D) and after (A) a re-breathing process; and determining an alveolar partial pressure of carbon dioxide ($PACO_2$) of the patient before, during and after said re-breathing process.

33. The method of claim 32, further comprising determining a time (t) of each of said before ($t_B$), said during ($t_D$), and said after ($t_A$) said re-breathing process.

34. The method of claim 33, further comprising calculating said rate of change by employing the following equation:

$$k = \frac{\Delta V_{CO_{2BD}} \cdot \Delta C_A CO_{2DA} - \Delta V_{CO_{2DA}} \cdot \Delta C_A CO_{2BD}}{\Delta V_{CO_{2BD}}(t_D - t_A) - \Delta V_{CO_{2DA}}(t_B - t_D)}.$$

35. A method of determining a change in carbon dioxide content of venous blood of a patient, comprising:

measuring a carbon dioxide elimination ($VCO_2$) of the patient before (B), during (D) and after (A) a re-breathing process; and determining an alveolar partial pressure of carbon dioxide ($PACO_2$) of the patient before, during and after said re-breathing process.

36. The method of claim 35, further comprising determining a time (t) of each of said before ($t_B$), said during ($t_D$), and said after ($t_A$) said re-breathing process.

37. The method of claim 36, further comprising calculating a rate of change by employing the following equation:

$$k = \frac{\Delta V_{CO_{2BD}} \cdot \Delta C_A CO_{2DA} - \Delta V_{CO_{2DA}} \cdot \Delta C_A CO_{2BD}}{\Delta V_{CO_{2BD}}(t_D - t_A) - \Delta V_{CO_{2DA}}(t_B - t_D)}.$$

38. The method of claim 37, further comprising calculating a change in a carbon dioxide content of venous blood of the patient from $t_B$ to $t_D$ ($\Delta CvCO_{2BD}$) by employing the following equation:

$$\Delta CvCO_{2BD} = k(t_B - t_D).$$

39. The method of claim 37, further comprising calculating a change in a carbon dioxide content of venous blood of the patient from $t_D$ to $t_A$ ($\Delta CvCO_{2DA}$) by employing the following equation:

$$\Delta CvCO_{2DA} = k(t_B - t_D).$$

40. A method of non-invasively determining pulmonary capillary blood flow of a patient, comprising:

measuring a before carbon dioxide elimination and a before partial pressure of end tidal carbon dioxide prior to a change in effective ventilation;

measuring a during carbon dioxide elimination and a during partial pressure of end tidal carbon dioxide during said change in effective ventilation; and measuring an after carbon dioxide elimination and an after partial pressure of end tidal carbon dioxide after said change in effective ventilation.

41. The method of claim 40, wherein said change in effective ventilation comprises re-breathing.

42. The method of claim 40, wherein said change in effective ventilation comprises a change in a respiratory rate.

43. The method of claim 40, wherein said change in effective ventilation comprises a change in an inspiratory time.

44. The method of claim 40, wherein said change in effective ventilation comprises a change in an expiratory time.

45. The method of claim 40, wherein said change in effective ventilation comprises a change in a tidal volume.

46. The method of claim 40, wherein said change in effective ventilation comprises a change in a quantity of carbon dioxide.

47. The method of claim 40, further comprising determining a rate of change of a carbon dioxide content of venous blood of the patient.

48. The method of claim 47, further comprising:

determining a before alveolar content of carbon dioxide from said before partial pressure of end tidal carbon dioxide;

determining a during alveolar content of carbon dioxide from said during partial pressure of end tidal carbon dioxide; and determining an after alveolar content of carbon dioxide from said after partial pressure of end tidal carbon dioxide.

49. The method of claim 48, further comprising:

determining a before time of said before carbon dioxide elimination;

determining a during time of said during carbon dioxide elimination; and determining an after time of said after carbon dioxide elimination.

50. The method of claim 47, further comprising:

determining a before time of said before partial pressure of end tidal carbon dioxide;

determining a during time of said during partial pressure of end tidal carbon dioxide; and determining an after time of said after partial pressure of end tidal carbon dioxide.

51. The method of claim 48, further comprising:

calculating said rate of change by employing the following equation:

$$k = \frac{\Delta V_{CO_2BD} \cdot \Delta C_A CO_{2DA} - \Delta V_{CO_2DA} \cdot \Delta C_A CO_{2BD}}{\Delta V_{CO_2BD}(t_D - t_A) - \Delta V_{CO_2DA}(t_B - t_D)},$$

where $\Delta VCO_{2BD}$ comprises a difference between said before carbon dioxide elimination and said during carbon dioxide elimination, $\Delta CACO_{2DA}$ comprises a difference between said during alveolar content and said after alveolar content, $\Delta VCO_{2DA}$ comprises a difference between said during carbon dioxide elimination and said after carbon dioxide elimination, $\Delta CACO_{2BD}$ comprises a difference between said before alveolar content and said during alveolar content, $t_B$ comprises a time of prior to said phase, $t_D$ comprises a time during said change, and $t_A$ comprises a time after said change.

52. The method of claim 48, further comprising calculating pulmonary capillary blood flow with said before carbon dioxide elimination, said during carbon dioxide elimination, said after carbon dioxide elimination, said before alveolar content, said during alveolar content, said after alveolar content, and said rate of change.

53. The method of claim 49, further comprising calculating pulmonary capillary blood flow with said before carbon dioxide elimination, said during carbon dioxide elimination, said after carbon dioxide elimination, said before alveolar content, said during alveolar content, said after alveolar content, said before time, said during time, said after time, and said rate of change.

54. The method of claim 52, further comprising calculating said pulmonary capillary blood flow by employing the following equation:

$$Q_{pcbf} = \frac{V_{CO_2B} + V_{CO_2A} - 2V_{CO_2D}}{k \cdot (t_B + t_A - 2t_D) - (C_A CO_{2B} + C_A CO_{2A} - 2C_A CO_{2D})}.$$

55. The method of claim 47, wherein said rate of change is substantially constant.

56. The method of claim 47, wherein said rate of change is substantially exponential over time.

57. The method of claim 40, further comprising:

determining a before time of said before carbon dioxide elimination;

determining a during time of said during carbon dioxide elimination; and determining an after time of said after carbon dioxide elimination.

58. The method of claim 57, wherein a difference between said during time and said before time is equal to a difference between said after time and said during time.

59. The method of claim 58, further comprising calculating pulmonary capillary blood flow by employing the following equation:

$$Q_{pcbf} = \frac{V_{CO_2B} + C_{CO_2A} - 2V_{CO_2D}}{-(C_A CO_{2B} + C_A CO_{2A} - 2C_A CO_{2D})}.$$

* * * * *

UNITED STATES PATENT AND TRADEMARK OFFICE
CERTIFICATE OF CORRECTION

PATENT NO. : 6,200,271 B1
DATED : March 13, 2001
INVENTOR(S) : Kai Kück et al.

It is certified that error appears in the above-identified patent and that said Letters Patent is hereby corrected as shown below:

Column 1,
Line 60, In the equation, change "$VO_2$" to -- $V_{O_2}$ --
Line 62, change "$VO_2$" to -- $V_{O_2}$ --

Column 2,
Lines 6, 14 and 22, change "$VO_2$" to -- $V_{O_2}$ --
Line 24, change "$FiO_2$" to -- $Fi_{O_2}$ --
Line 28, change "$(VCO_2)$" to -- $(V_{CO_2})$ --
Lines 29 and 49, change "$VCO_2$" to -- $V_{CO_2}$ --
Line 33, change "$VCO_2$" to -- $V_{CO_2}$ -- and change "$VO_2$" to -- $V_{O_2}$ --
Line 37, In the equation, change "$VO_2$" to -- $V_{O_2}$ -- and change "$VCO_2$" to -- $V_{CO_2}$ --
Line 47, In the equation, change "$VCO_2$" to -- $V_{CO_2}$ --

Column 3,
Lines 3 and 57, change "$(PACO_2)$" to -- $(P_{ACO_2})$ --

Column 4,
Line 11, change "$(VCO_2)$" to -- $(V_{CO_2})$ --
Line 13, change "$(CACO_2)$" to -- $(C_{ACO_2})$ --
Line 20, change "$VCO_{2B}$" to -- $V_{CO_{2B}}$ -- and change "$VCO_{2D}$" to -- $V_{CO_{2D}}$ --
Line 25, change "$CACO_{2B}$" to -- $C_{ACO_{2B}}$ -- and change "$CACO_{2D}$" to -- $C_{ACO_{2D}}$ --
Line 41, change "$VCO_2$" to -- $V_{CO_2}$ --
Line 63, change "$(VCO_2)$" to -- $(V_{CO_2})$ -- and change "$(VCO_{2B})$" to -- $(V_{CO_{2B}})$ -- and change "$(VCO_{2D})$" to -- $(V_{CO_{2D}})$ --
Line 64, change "$(VCO_{2A})$" to -- $(V_{CO_{2A}})$ --

Column 5,
Line 14, change ""$\Delta VCO_{2BD}$"," to -- "$\Delta V_{CO_{2BD}}$", --
Line 16, change ""$\Delta VCO_{2DA}$"," to -- "$\Delta V_{CO_{2DA}}$", --
Line 19, change ""$\Delta CACO_{2BD}$"," to -- "$\Delta C_{ACO_{2BD}}$", --
Line 20, change "alter" to -- after --
Line 21, change ""$\Delta CACO_{2DA}$"," to -- "$\Delta C_{ACO_{2DA}}$", --
Lines 49 and 55, change "$VCO_2$" to -- $V_{CO_2}$ --

Column 6,
Line 12, change "$VCO_2$" to -- $V_{CO_2}$ --

UNITED STATES PATENT AND TRADEMARK OFFICE
CERTIFICATE OF CORRECTION

PATENT NO. : 6,200,271 B1
DATED : March 13, 2001
INVENTOR(S) : Kai Kück et al.

It is certified that error appears in the above-identified patent and that said Letters Patent is hereby corrected as shown below:

Column 8,
Lines 29-30, change the equation in its entirety to -- $\Delta V_{CO_{2BD}} \cdot \Delta C_{vCO_{2DA}} - \Delta V_{CO_{2DA}} \cdot \Delta C_{vCO_{2BD}} = \Delta V_{CO_{2BD}} \cdot \Delta C_{ACO_{2DA}} - \Delta V_{CO_{2DA}} \cdot \Delta C_{ACO_{2BD}}$. --
Lines 35-36, in the equation, change "$\Delta VCO_{2BD}$" (both occurrences) to
-- $\Delta V_{CO_{2BD}}$ --; change "$\Delta VCO_{2DA}$" (both occurrences) to -- $\Delta V_{CO_{2DA}}$ --; change
"$\Delta C_ACO_{2DA}$" to -- $\Delta C_ACO_{2DA}$ --; and change "$\Delta C_ACO_{2BD}$" to -- $\Delta C_ACO_{2BD}$ --
Line 39, change "VCO$_2$" to -- $V_{CO_2}$ --

Column 9,
Lines 29 and 55, change "VCO$_2$" to -- $V_{CO_2}$ --
Line 56, change "CACO$_2$" to -- $C_ACO_2$ --

Column 10,
Lines 2 and 15, change "VCO$_2$" to -- $V_{CO_2}$ --
Line 9, change "CACO$_2$" to -- $C_ACO_2$ --
Line 13, change "(VCO$_2$)" to -- ($V_{CO_2}$) -- and change "(VCO$_{2B}$)" to -- ($V_{CO_{2B}}$) --
Line 14, change "(VCO$_{2D)}$" to -- ($V_{CO_{2D}}$ -- and change "(VCO$_{2A)}$" to -- ($V_{CO_{2A}}$) --
Line 23, change "PACO$_2$" to -- $P_ACO_2$ --
Line 26, change "(CACO$_2$)" to -- ($C_ACO_2$) --
Line 37, change ""$\Delta VCO_{2BD}$",", to -- "$\Delta V_{CO_{2BD}}$", --
Line 39, change ""$\Delta VCO_{2DA}$",", to -- "$\Delta V_{CO_{2DA}}$", --
Line 42, change ""$\Delta CACO_{2BD}$",", to -- "$\Delta C_ACO_{2BD}$", --
Line 44, change ""$\Delta CACO_{2DA}$",", to -- "$\Delta C_ACO_{2DA}$", --

Column 12,
Line 2, in the equation "$\Delta C_ACO_{2DA}$" to -- $\Delta C_ACO_{2DA}$ -- and change "$\Delta C_ACO_{2BD}$"
to -- $\Delta C_ACO_{2BD}$ --
Line 6, change "$\Delta VCO_{2BD}$" to -- $\Delta V_{CO_{2BD}}$ --
Line 9, change "$\Delta CACO_{2DA}$" to -- $\Delta C_ACO_{2DA}$ --
Line 11, change "$\Delta VCO_{2DA}$" to -- $\Delta V_{CO_{2DA}}$ --
Line 12, change "$\Delta CACO_{2BD}$" to -- $\Delta C_ACO_{2BD}$ --

Column 13,
Line 2, change "(VCO$_{2B)}$" to -- ($V_{CO_{2B}}$) --
Line 3, change "(PACO$_{2B}$)" to -- ($P_ACO_{2B}$) --
Line 6, change "(VCO$_{2D}$)" to -- ($V_{CO_{2D}}$) --
Line 8, change "(PACO$_{2D}$)" to -- ($P_ACO_{2D}$) --
Line 10, change "(VCO$_{2A}$)" to -- ($V_{CO_{2A}}$) --
Line 11, change "(PACO$_{2A}$)" to -- ($P_ACO_{2A}$) --
Line 45, change "(VCO$_2$)" to -- ($V_{CO_2}$) --
Line 49, change "(PACO$_2$)" to -- ($P_ACO_2$) --

UNITED STATES PATENT AND TRADEMARK OFFICE
CERTIFICATE OF CORRECTION

PATENT NO. : 6,200,271 B1
DATED : March 13, 2001
INVENTOR(S) : Kai Kück et al.

It is certified that error appears in the above-identified patent and that said Letters Patent is hereby corrected as shown below:

Column 14,
Lines 20 and 38, change "($VCO_2$)" to -- ($Vco_2$) --
Lines 24 and 42, change "($PACO_2$)" to -- ($PaCO_2$) --

Column 16,
Line 6, change "$\Delta VCO_{2BD}$" to -- $\Delta Vco_{2BD}$ --
Line 8, change "$\Delta CACO_{2DA}$" to -- $\Delta CaCO_{2DA}$ --
Line 10, change "$\Delta VCO_{2DA}$" to -- $\Delta Vco_{2DA}$ --
Line 13, change "$\Delta CACO_{2BD}$" to -- $\Delta CaCO_{2BD}$ --
Line 15, change "phase" to -- change --

Signed and Sealed this

Twenty-fourth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,200,271 B1
DATED : March 13, 2001
INVENTOR(S) : Kai Kück et al.

It is certified that error appears in the above-identified patent and that said Letters Patent is hereby corrected as shown below:

Column 1,
Line 60, In the equation, change "VO$_2$" to -- V$o_2$ --
Line 62, change "VO$_2$" to -- V$o_2$ --

Column 2,
Lines 6, 14 and 22, change "VO$_2$" to -- V$o_2$ --
Line 24, change "FiO$_2$" to -- Fi$o_2$ --
Line 28, change "(VCO$_2$)" to -- (V$co_2$) --
Lines 29 and 49, change "VCO$_2$" to -- V$co_2$ --
Line 33, change "VCO$_2$" to -- V$co_2$ -- and change "VO$_2$" to -- V$o_2$ --
Line 37, In the equation, change "VO$_2$" to -- V$o_2$ -- and change "VCO$_2$" to -- V$co_2$ --
Line 47, In the equation, change "VCO$_2$" to -- V$co_2$ --

Column 3,
Lines 3 and 57, change "(PACO$_2$)" to -- (P$a$CO$_2$) --

Column 4,
Line 11, change "(VCO$_2$)" to -- (V$co_2$) --
Line 13, change "(CACO$_2$)" to -- (C$a$CO$_2$) --
Line 20, change "VCO$_{2B}$" to -- V$co_{2B}$ -- and change "VCO$_{2D}$" to -- V$co_{2D}$ --
Line 25, change "CACO$_{2B}$" to -- C$a$CO$_{2B}$ -- and change "CACO$_{2D}$" to
-- C$a$CO$_{2D}$ --
Line 41, change "VCO$_2$" to -- V$co_2$ --
Line 63, change "(VCO$_2$)" to -- (V$co_2$) -- and change "(VCO$_{2B}$)" to -- (V$co_{2B}$) -- and change "(VCO$_{2D}$)" to -- (V$co_{2D}$) --
Line 64, change "(VCO$_{2A}$)" to -- (V$co_{2A}$) --

Column 5,
Line 14, change ""ΔVCO$_{2BD}$","" to -- "ΔV$co_{2BD}$", --
Line 16, change ""ΔVCO$_{2DA}$","" to -- "ΔV$co_{2DA}$", --
Line 19, change ""ΔCACO$_{2BD}$","" to -- "ΔC$a$CO$_{2BD}$", --
Line 20, change "alter" to -- after --
Line 21, change ""ΔCACO$_{2DA}$","" to -- "ΔC$a$CO$_{2DA}$", --
Lines 49 and 55, change "VCO$_2$" to -- V$co_2$ --

Column 6,
Line 12, change "VCO$_2$" to -- V$co_2$ --

UNITED STATES PATENT AND TRADEMARK OFFICE
CERTIFICATE OF CORRECTION

PATENT NO. : 6,200,271 B1
DATED : March 13, 2001
INVENTOR(S) : Kai Kück et al.

It is certified that error appears in the above-identified patent and that said Letters Patent is hereby corrected as shown below:

Column 8,
Lines 29-30, change the equation in its entirety to -- $\Delta V{CO_2}_{BD} \cdot \Delta C v{CO_2}_{DA} - \Delta V{CO_2}_{DA} \cdot \Delta C v{CO_2}_{BD} = \Delta V{CO_2}_{BD} \cdot \Delta C a{CO_2}_{DA} - \Delta V{CO_2}_{DA} \cdot \Delta C a{CO_2}_{BD}$. --
Lines 35-36, in the equation, change "$\Delta V{CO_2}_{BD}$" (both occurrences) to -- $\Delta V{CO_2}_{BD}$ --; change "$\Delta V{CO_2}_{DA}$" (both occurrences) to -- $\Delta V{CO_2}_{DA}$ --; change "$\Delta C_A{CO_2}_{DA}$" to -- $\Delta C a{CO_2}_{DA}$ --; and change "$\Delta C_A{CO_2}_{BD}$" to -- $\Delta C a{CO_2}_{BD}$ --
Line 39, change "$V{CO_2}$" to -- $V{CO_2}$ --

Column 9,
Lines 29 and 55, change "$V{CO_2}$" to -- $V{CO_2}$ --
Line 56, change "$C a{CO_2}$" to -- $C a{CO_2}$ --

Column 10,
Lines 2 and 15, change "$V{CO_2}$" to -- $V{CO_2}$ --
Line 9, change "$C a{CO_2}$" to -- $C a{CO_2}$ --
Line 13, change "$(V{CO_2})$" to -- $(V{CO_2})$ -- and change "$(V{CO_2}_B)$" to -- $(V{CO_2}_B)$ --
Line 14, change "$(V{CO_2}_D)$" to -- $(V{CO_2}_D)$ -- and change "$(V{CO_2}_A)$" to -- $(V{CO_2}_A)$ --
Line 23, change "$P a{CO_2}$" to -- $P a{CO_2}$ --
Line 26, change "$(C a{CO_2})$" to -- $(C a{CO_2})$ --
Line 37, change ""$\Delta V{CO_2}_{BD}$","  to -- "$\Delta V{CO_2}_{BD}$", --
Line 39, change ""$\Delta V{CO_2}_{DA}$","  to -- "$\Delta V{CO_2}_{DA}$", --
Line 42, change ""$\Delta C a{CO_2}_{BD}$","  to -- "$\Delta C a{CO_2}_{BD}$", --
Line 44, change ""$\Delta C a{CO_2}_{DA}$","  to -- "$\Delta C a{CO_2}_{DA}$", --

Column 12,
Line 2, in the equation "$\Delta C_A{CO_2}_{DA}$" to -- $\Delta C a{CO_2}_{DA}$ -- and change "$\Delta C_A{CO_2}_{BD}$" to -- $\Delta C a{CO_2}_{BD}$ --
Line 6, change "$\Delta V{CO_2}_{BD}$" to -- $\Delta V{CO_2}_{BD}$ --
Line 9, change "$\Delta C a{CO_2}_{DA}$" to -- $\Delta C a{CO_2}_{DA}$ --
Line 11, change "$\Delta V{CO_2}_{DA}$" to -- $\Delta V{CO_2}_{DA}$ --
Line 12, change "$\Delta C a{CO_2}_{BD}$" to -- $\Delta C a{CO_2}_{BD}$ --

Column 13,
Line 2, change "$(V{CO_2}_B)$" to -- $(V{CO_2}_B)$ --
Line 3, change "$(P a{CO_2}_B)$" to -- $(P a{CO_2}_B)$ --
Line 6, change "$(V{CO_2}_D)$" to -- $(V{CO_2}_D)$ --
Line 8, change "$(P a{CO_2}_D)$" to -- $(P a{CO_2}_D)$ --
Line 10, change "$(V{CO_2}_A)$" to -- $(V{CO_2}_A)$ --
Line 11, change "$(P a{CO_2}_A)$" to -- $(P a{CO_2}_A)$ --
Line 45, change "$(V{CO_2})$" to -- $(V{CO_2})$ --
Line 49, change "$(P a{CO_2})$" to -- $(P a{CO_2})$ --

UNITED STATES PATENT AND TRADEMARK OFFICE
CERTIFICATE OF CORRECTION

PATENT NO.    : 6,200,271 B1
DATED         : March 13, 2001
INVENTOR(S)   : Kai Kück et al.

It is certified that error appears in the above-identified patent and that said Letters Patent is hereby corrected as shown below:

Column 14,
Lines 20 and 38, change "($VCO_2$)" to -- ($V_{CO_2}$) --
Lines 24 and 42, change "($PACO_2$)" to -- ($P_ACO_2$) --

Column 16,
Line 6, change "$\Delta VCO_{2BD}$" to -- $\Delta V_{CO_{2BD}}$ --
Line 8, change "$\Delta CACO_{2DA}$" to -- $\Delta C_ACO_{2DA}$ --
Line 10, change "$\Delta VCO_{2DA}$" to -- $\Delta V_{CO_{2DA}}$ --
Line 13, change "$\Delta CACO_{2BD}$" to -- $\Delta C_ACO_{2BD}$ --
Line 15, change "phase" to -- change --

Signed and Sealed this

Fifteenth Day of July, 2003

JAMES E. ROGAN
*Director of the United States Patent and Trademark Office*